United States Patent
Tao

(10) Patent No.: US 12,065,662 B2
(45) Date of Patent: Aug. 20, 2024

(54) APPLICATION OF LENTIVIRAL VECTOR EF1α PROMOTER FOR OPTIMISING ABCD1 GENE EXPRESSION TO TREAT ADRENOLEUKODYSTROPHY

(71) Applicant: Chengdu Youwa Biotechnology Co., Ltd., Sichuan (CN)

(72) Inventor: Ran Tao, Sichuan (CN)

(73) Assignee: Chengdu Youwa Biotechnology Co., Ltd., Sichuan (CN)

(*) Notice: Subject to any disclaimer, the term of this patent is extended or adjusted under 35 U.S.C. 154(b) by 757 days.

(21) Appl. No.: 17/042,751

(22) PCT Filed: May 24, 2019

(86) PCT No.: PCT/CN2019/088225
§ 371 (c)(1),
(2) Date: Sep. 28, 2020

(87) PCT Pub. No.: WO2019/185067
PCT Pub. Date: Oct. 3, 2019

(65) Prior Publication Data
US 2022/0228166 A1    Jul. 21, 2022

(30) Foreign Application Priority Data
Mar. 29, 2018 (CN) .................. 201810275166.2

(51) Int. Cl.
| C12N 15/86 | (2006.01) |
| A61K 35/28 | (2015.01) |
| A61K 48/00 | (2006.01) |
| A61P 25/00 | (2006.01) |
| C12N 9/16 | (2006.01) |

(52) U.S. Cl.
CPC .......... *C12N 15/86* (2013.01); *A61K 35/28* (2013.01); *A61K 48/0066* (2013.01); *A61P 25/00* (2018.01); *C12N 9/16* (2013.01); *C12Y 301/02* (2013.01); *C12N 2740/15043* (2013.01)

(58) Field of Classification Search
None
See application file for complete search history.

(56) References Cited

U.S. PATENT DOCUMENTS 8,858,928 B2   10/2014 Denaro et al.
9,061,031 B2 *  6/2015 Denaro ............. A61K 48/0058

FOREIGN PATENT DOCUMENTS

| CN | 1429911 A | 7/2003 |
| CN | 103717240 A | 4/2014 |
| CN | 108456697 A | 8/2018 |
| WO | 2012159120 A2 | 11/2012 |

OTHER PUBLICATIONS

Uetseki et al. Isolation and Characterization of the Human Chromosomal Gene for Polypeptide Chain Elongation Factorl. The Journal of Biological Chemistry (1989), 264(10), 5791-5798. (Year: 1989).*
Office Action for corresponding Chinese Application No. 20181075166.2.
Chang et al., "Lentiviral siRNAs targeting multiple highly conserved RNA sequences of human immunodeficiency virus type 1", Gene Therapy (2005) 12, 1133-1144.
Zhang et al., "Construction and expression of Lentiviral vector containing adrenoleukodystrophy gene", Academic Journal of Second Military Medical University, Aug. 2014, vol. 35, No. 8.
International Search Report for corresponding PCT Application No. PCT/CN2019/088225 mailed Aug. 21, 2019.
Meng et al., "Advances of Lentiviral Vectors", Chin J Lung Cancer, Dec. 2014, vol. 17, No. 12, p. 870-876.
Cartier et al., "Hematopoietic Stem Cell Gene Therapy with a Lentiviral Vector in X-Linked Adrenoleukodystrophy", Science 326 (5954), 818-823, DOI: 10.1126/science.1171242.

* cited by examiner

*Primary Examiner* — Sean C. Barron
(74) *Attorney, Agent, or Firm* — Wood, Phillips, Katz, Clark & Mortimer

(57) ABSTRACT

Provided is a lentiviral vector comprising an EF1α promoter, a normal ABCD1 gene and an NHP/TYF lentiviral vector system, said vector being used for treating adrenoleukodystrophy. The present invention uses transfection into autologous haematopoietic stem cells (HSCs), for ALD gene therapy after being returned, which may be performed in combination with direct intracerebral injection of the lentiviral vector carrying the ABCD1 gene according to the actual circumstances.

3 Claims, 3 Drawing Sheets

Specification includes a Sequence Listing.

May-December 2015 Clinical Trial Cases

| Patient | Disease | Transgene | Wt./KG | Age | HSC | MSC |
|---------|---------|-----------|--------|-----|-----|-----|
| G001 | MLD | ARSA | 16 | 4 | $1.3 \times 10^8$ | $1.0 \times 10^8$ |
| G002 | ALD | ABCD1 | 28 | 10 | $3.0 \times 10^8$ | $5.7 \times 10^7$ |
| G003 | ALD | ABCD1 | 20 | 7 | $6.6 \times 10^7$ | $1.0 \times 10^8$ |
| G004 | MLD | ARSA | 30 | 12 | $1.3 \times 10^8$ | $3.8 \times 10^7$ |
| G005 | MLD | ARSA | 12 | 2.5 | $1.8 \times 10^7$ | $7.0 \times 10^7$ |
| G006 | ALD | ABCD1 | 19 | 6 | $8.0 \times 10^6$ | $3.9 \times 10^7$ |
| G007 | ALD | ABCD1 | 23 | 6 | $4.3 \times 10^7$ | $6.2 \times 10^7$ |
| G008 | ALD | ABCD1 | 20 | 5 | $1.9 \times 10^8$ | $5.3 \times 10^7$ |
| G009 | ALD | ABCD1 | 24 | 9 | $2.2 \times 10^8$ | $5.0 \times 10^7$ |
| G010 | ALD | ABCD1 | 44 | 13 | $1.7 \times 10^8$ | $8.0 \times 10^7$ |

Figure 4

APPLICATION OF LENTIVIRAL VECTOR EF1α PROMOTER FOR OPTIMISING ABCD1 GENE EXPRESSION TO TREAT ADRENOLEUKODYSTROPHY

TECHNICAL FIELD

The present application belongs to the field of gene engineering and, in particular, to an application of a lentiviral vector EF1α promoter for optimizing ABCD1 gene expression to treat adrenoleukodystrophy.

BACKGROUND

Adrenoleukodystrophy (ALD) is a recessive inherited lipid metabolic disease. This disease is caused by the massive accumulation of very long chain fatty acid (VLCFA) in organs and tissues such as blood, brain white matter, adrenal cortex due to dysfunction of peroxisomes in oxidating VLCFA in cells, resulting in central nervous system demyelination and adrenocortical atrophy or dysplasia. ALD is the most common peroxisomal disease, and mainly affects adrenal glands and cerebral white matter. More than half of patients start to suffer from this disease in their childhood or adolescence. The disease is mainly characterized by progressive psychomotor disorders, visual loss and hearing loss, and/or adrenal hypofunction. The incidence of this disease is about 0.5/100,000 to 1/100,000, 95% in male and 5% for female heterozygote. There is no region specificity and race specificity.

Since ALD is a disease caused by monogenic mutations, gene therapy can theoretically achieve complete treatment of this disease. Hematopoietic stem cells (HSCs) and mesenchymal stem cells (MSCs) have several characteristics that make them potential "vehicles" for gene therapy. HSCs and MSCs can be obtained from blood or bone marrow, and have the ability to differentiate into a series of somatic cells and update various tissue cells. However, if the ABCD1 gene expression is low in cells, the abnormal accumulation of VLCFA in cytoplasm could not be effectively removed.

Although there are various gene therapy methods for gene transfer by using viral vectors at home and abroad, the gene transfer efficiency is greatly different due to different viral vectors or even different preparation methods for the same vector, and the gene transfer efficiency directly affects the disease therapeutic effect. Most of the existing methods for treating genetic diseases by using cell therapy have much low efficiency and only modify blood stem cells, so that the clinical effect of disease treatment is not as expected. Therefore, a method for improving the viral gene transfer efficiency to the maximum extent and modifying various stem cells to improve the therapeutic effect of genetic diseases is urgently needed.

Conducted by BlueBird Bio (U.S.) and other institutes, clinical trials of gene therapy for 17 children suffering from ALD by using lentiviral vectors carrying normal ABCD1 genes are now in the data collection stage. Currently, the results show that a certain response effect to the therapy within two years occurs in patients, but the overall effect is still weak. Among patients, one patient loses his ability to act and speak, and the other cases are still under observation, so gene therapy for ALD disease is currently in the initial stage.

SUMMARY

The method provided by the solution of the present application is mainly to realize ALD gene therapy by transfecting autologous hematopoietic stem cells (HSCs) of a patient with an improved and optimized lentiviral vector carrying an ABCD1 gene under an EF1α promoter, where it may be carried out in combination with direct intracerebral injection of lentiviral vector carrying the ABCD1 gene according to actual conditions. The specific components of the carrier protein, the optimization and improvement of the packaging cells and purification mode are all directionally designed. Any other cases using same modified systems shall be considered as infringement, including changes of the promoter (such as replacing EF1α with CMV to realize gene expression), shortening of the length of ABCD1 proteins (such as using only partial sequences of functional domains) and addition of any meaningless protein to the lentiviral vector on the basis of this system.

One aspect of the present application discloses a lentiviral vector containing a recombinant plasmid and a preparation method thereof. The present application mainly optimizes the lentiviral vector itself and packaging and purification methods for ABCD1 gene expression. And, various stem cells are used as delivery vectors, so that the gene has high expression efficiency in differentiated or undifferentiated stem cells. The expression level of the ABCD1 gene in transgenic cells is significantly increased after optimization of the lentiviral vector. In addition, the lentiviral vector adopted in the present application is an updated gene transfer system, which allows, under the initiation of the EF1α promoter, more efficient gene transfer while ensuring safety. The lentiviral vector adopted in the present application is an optimized and improved gene transfer system, and compared with other previous systems, this system has higher transfection efficiency, stronger stability, and better safety, and can complete the transfer of normal genes more efficiently in the hemophilia gene therapy process. With transduction through this system, stable expression of the ABCD1 gene in HSCs and MSCs can be successfully realized, fully proving the feasibility of the present application on successful hemophilia gene therapy.

The present application provides a lentiviral vector carrying a normal ABCD1 gene, including an ABCD1 gene sequence, a human EF1a promoter sequence and an NHP/TYF lentiviral vector system.

The NHP/TYF lentiviral vector system includes vectors pNHP, pTYF and pHEF-VSV-G.

Another aspect of the present application discloses a stem cell system modified with the lentiviral vector. The sequence of the ABCD1 gene is shown in SEQ ID NO.1. The recombinant plasmid is an EF1a promoter sequence shown in SEQ ID NO.3 followed by the ABCD1 gene sequence shown in SEQ ID No.1. The lentiviral vector is obtained by connecting the recombinant plasmid to a lentiviral vector, followed by packaging, purifying and concentrating. The lentiviral vector-modified dual stem cell system is to transfect one or two kinds of peripheral hematopoietic stem cells or mesenchymal stem cells respectively with the lentiviral vector, and preferably, simultaneously transfect hematopoietic stem cells and mesenchymal stem cells to obtain a dual stem cell system which can stably express the ABCD1 gene.

The present application has the following advantages: The dual stem cells are modified with the lentiviral vector such that the stem cells can stably and massively express the ABCD1 gene, laying an important foundation for better improving the therapeutic effect of ALD treatment. In addition, with respect to treatment manners, according to the actual conditions of the patient, the present solution adopts a treatment means combined with a mode of transfecting the dual stem cells with the lentiviral vector carrying the ABCD1 gene and injecting the dual stem cells back intravenously, which is of important significance to realize the quicker ALD symptom relief and the more comprehensive and durable gene treatment. Therefore, in the present application, the ALD gene therapy is subjected to vector optimization and transgenic efficiency improvement, and compared with methods only using a stem cell line for treatment, this method uses the dual stem cell lines for treatment and thus can effectively improve the transfer efficiency and the expression level activity of the ABCD1 gene, and is of important significance to guarantee the effectiveness of gene therapy.

BRIEF DESCRIPTION OF DRAWINGS

FIG. 4 is clinical case records of ALD treatment using dual stem cells (hematopoietic stem cells (HSCs) and mesenchymal stem cells (MSCs)) obtained through transfection with the lentiviral vector carrying the normal ABCD1.

DETAILED DESCRIPTION

To further elaborate on the technical means adopted and the effects achieved in the present application, the technical solutions of the present application are specifically described below through specific examples in conjunction with drawings, but the present application is not limited to the scope of the examples.

The contents without specific techniques or conditions specified in the examples are conducted according to technical conditions described in the literature widely recognized in the art or according to specifications of the corresponding products.

The reagents or instruments used herein without manufacturers specified are conventional products commercially available from proper channels.

Figure 1:
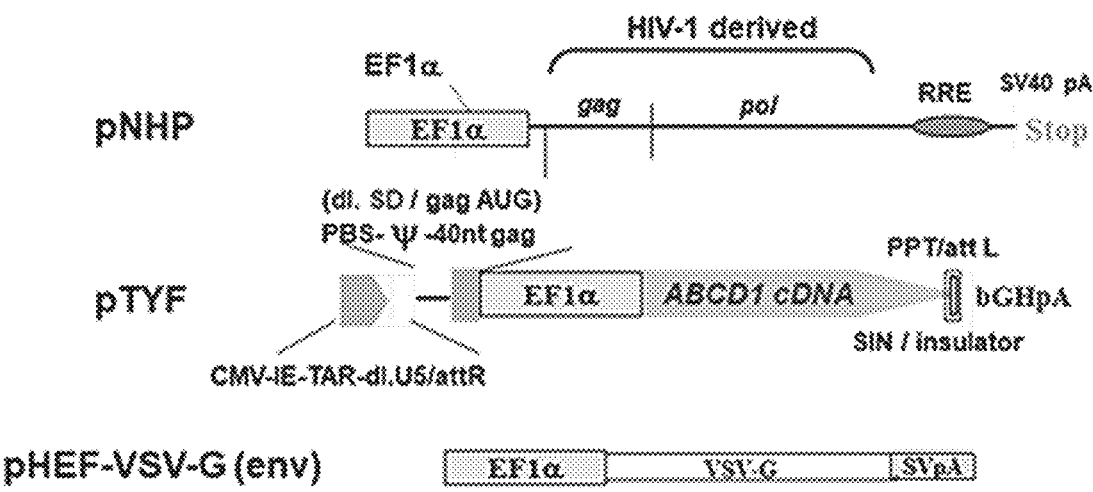
FIG. 1 is a schematic diagram illustrating the construction of a lentiviral vector and a production and purification process thereof.
Figure 1:
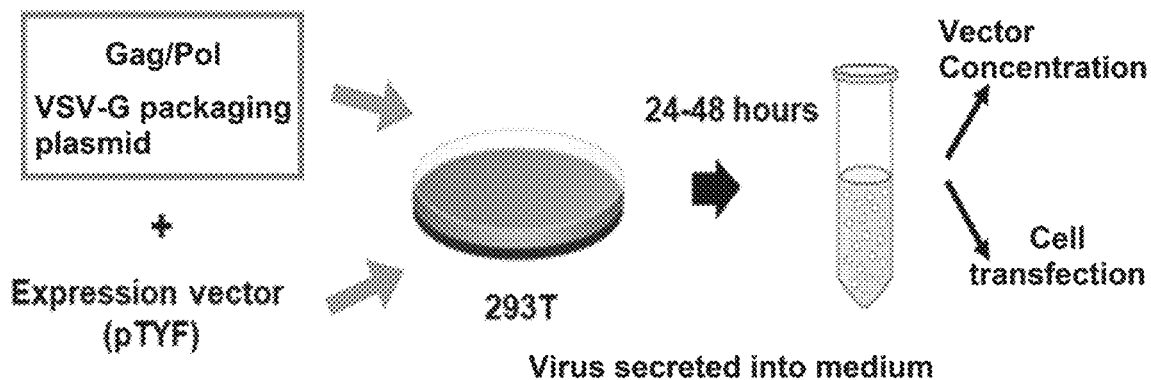

Example 1: Construction, Packaging and Purification of Lentiviral Vector Carrying Normal ABCD1 Gene A normal ABCD1 gene sequence (shown in SEQ ID NO. 1) and a human EF1α promoter sequence (shown in SEQ ID NO. 3) were synthesized through gene synthesis, and connected into a lentiviral vector (NHP/TYF lentiviral vector system) through restriction enzyme sites. The obtained product was identified through manners such as sequencing and double enzyme digestion (a BamHI cloning site ggatccacc-AUG was used for 5', and a SpeI site was used for 3' for cloning; and optimal reaction conditions were referred to the original NEB suggestion) to obtain a correctly connected lentiviral expression vector which carried a normal ABCD1 gene under the hEF1α promoter (shown in SEQ ID NO. 3). The specific connection locations and the construction of the lentiviral vector are shown in FIG. 1.

Figure 2:
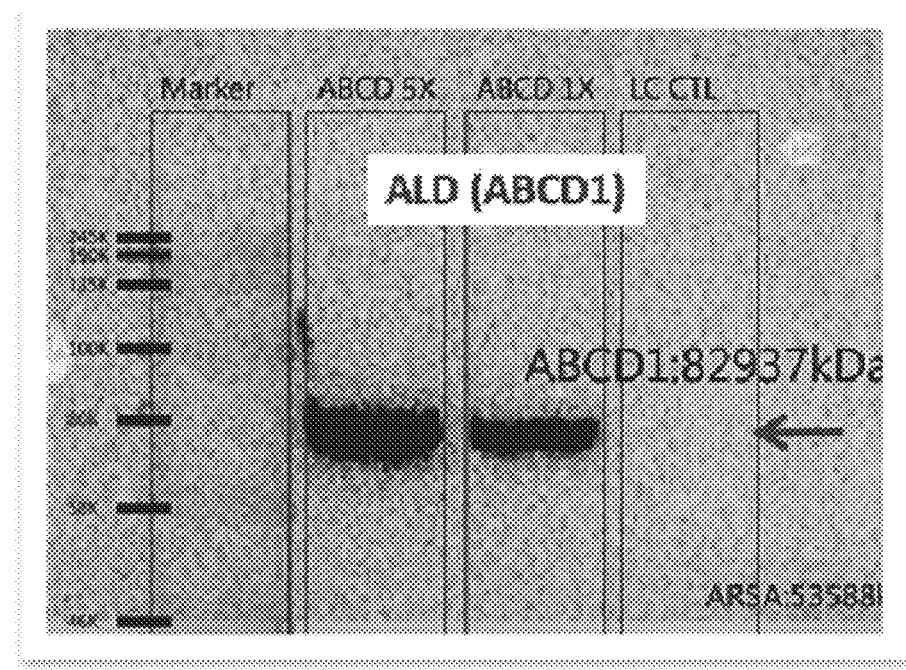
FIG. 2 illustrates protein identification of the protein expression level of the ABCD1 gene in stem cells.

After lentivirus were packaged, purified and concentrated and used to transfect stem cells, protein expression level of the ABCD1 gene in the stem cells was identified, as shown in FIG. 2. Protein expression level identification was performed on the collected HSCs which were transfected by the lentivirus carrying the normal ABCD1 gene to clarify the expression of the ABCD1 gene in HSCs. There was no ABCD1 protein expression in negative control HSCs that were not transfected by the lentivirus, whereas significantly high ABCD1 protein expression was found in the HSCs transfected by the lentivirus carrying the normal ABCD1 gene. The above shows that in the present application, the HSCs can massively express ABCD1 protein by means of the lentivirus, and has great disease treatment potential. The contents without specific techniques or conditions specified in the examples are conducted according to technical conditions described in the literature widely recognized in the art or according to specifications of the corresponding products. The reagents or instruments used herein without manufacturers specified are conventional products commercially available from proper channels.

Figure 3:
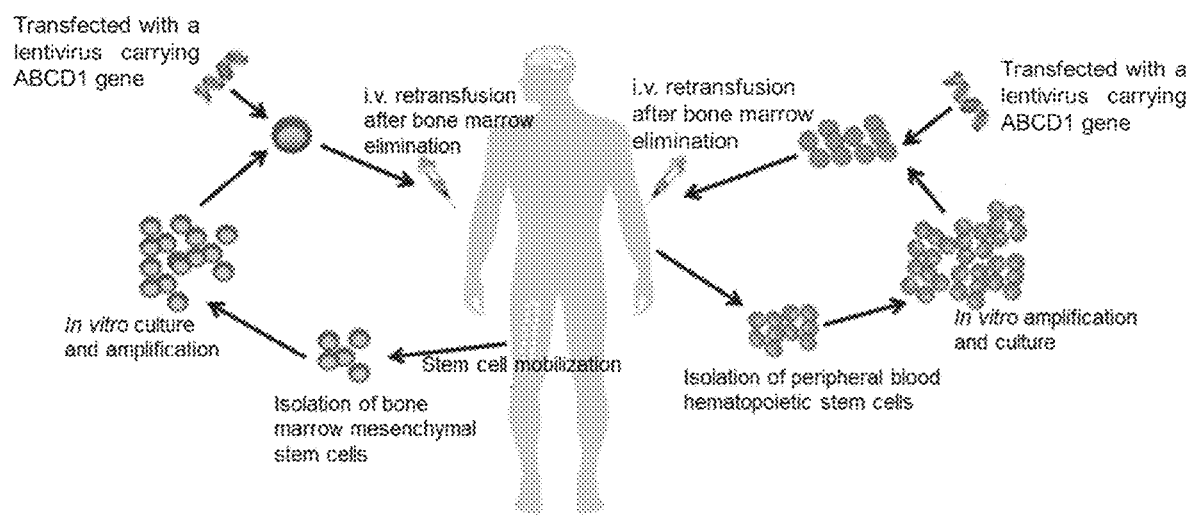
FIG. 3 is a schematic diagram illustrating a therapeutic procedure for treating ALD disease by using a dual stem cell system obtained through transfection with a lentiviral vector carrying a normal ABCD1.

In the present application, a therapeutic procedure for treating ALD disease by using a dual stem cell system obtained through transfection with a lentiviral vector carrying a normal ABCD1 is shown in FIG. 3. Stem cells of a patient are mobilized, then peripheral blood of the patient is collected, and hematopoietic stem cells and mesenchymal stem cells in the peripheral blood are isolated. The dual stem cells are transfected by a lentiviral vector carrying a normal ABCD1 gene to obtain stem cells carrying the normal ABCD1 gene. The cells are intravenously injected back into the patient for disease treatment. In clinical trials of autologous transplantation with gene therapy, 7 ALD patients and 3 MLD patients were treated by using the dual stem cells. The treatment process was smooth, the transplantation of the patients was good. The cell processing data is shown in FIG. 4.

The above are only preferred examples of the present application and are not intended to limit the present application in form or in substance, and for those skilled in the art, various equivalent changes such as variations, modifications and evolutions made in light of the above disclosed contents without departing from the solutions of the present application all are equivalent embodiments of the present application. Any various equivalent changes such as variations, modifications and evolutions made on the above examples in light of the above substantial techniques of the present application are within the scope of the present application.

The ASCII text file "Sequence.txt" created on Dec. 30, 2021, having the size of 17.4 kilobytes, is incorporated by reference into the specification.

What is claimed is:

1. A lentiviral vector carrying a normal ABCD1 gene, comprising an ABCD1 gene sequence, a human EF1α promoter sequence and a lentiviral vector NHP/TYF lentiviral vector system,
   wherein the lentiviral vector comprises the sequence of SEQ ID NO: 3.

2. The lentiviral vector carrying the normal ABCD1 gene according to claim 1,
   wherein the ABCD1 gene sequence and the human EF1a promoter sequence are connected into the lentiviral vector NHP/TYF lentiviral vector system through restriction enzyme sites.

3. A method for preparing a lentiviral vector carrying a normal ABCD1 gene, comprising: connecting an ABCD1 gene sequence and a human EF1a promoter sequence into a lentiviral vector NHP/TYF lentiviral vector system through restriction enzyme sites, followed by packaging, purification and concentration,
   wherein the human EF1a promoter sequence haslentiviral vector comprises the sequence of SEQ ID NO: 3.

* * * * *

UNITED STATES PATENT AND TRADEMARK OFFICE
CERTIFICATE OF CORRECTION

| | | |
|---|---|---|
| PATENT NO. | : 12,065,662 B2 | Page 1 of 1 |
| APPLICATION NO. | : 17/042751 | |
| DATED | : August 20, 2024 | |
| INVENTOR(S) | : Ran Tao | |

It is certified that error appears in the above-identified patent and that said Letters Patent is hereby corrected as shown below:

In the Claims

Claim 3, Column 16 Line 60-61:
wherein the human EF1a promoter sequence haslentiviral vector comprises the sequence of SEQ ID NO: 3.

Should be:
wherein the lentiviral vector comprises the sequence of SEQ ID NO: 3.

Signed and Sealed this
Seventeenth Day of June, 2025

Coke Morgan Stewart
*Acting Director of the United States Patent and Trademark Office*

SEQUENCE LISTING

<160> NUMBER OF SEQ ID NOS: 4

<210> SEQ ID NO 1
<211> LENGTH: 2238
<212> TYPE: DNA

<213> ORGANISM: Homo sapiens

<400> SEQUENCE: 1

| | | | | | |
|---|---|---|---|---|---|
| atgccggtgc | tctccaggcc | ccggccctgg | cgggggaaca | cgctgaagcg | cacggccgtg | 60 |
| ctcctggccc | tcgcggccta | tggagcccac | aaagtctacc | ccttggtgcg | ccagtgcctg | 120 |
| gccccggcca | ggggtcttca | ggcgcccgcc | ggggagccca | cgcaggaggc | ctccggggtc | 180 |
| gcggcggcca | aagctggcat | gaaccgggta | ttcctgcagc | ggctcctgtg | gctcctgcgg | 240 |
| ctgctgttcc | cccgggtcct | gtgccgggag | acggggctgc | tggccctgca | ctcggccgcc | 300 |
| ttggtgagcc | gcaccttcct | gtcggtgtat | gtggcccgcc | tggacggaag | gctggccgc | 360 |
| tgcatcgtcc | gcaaggaccc | gcgggctttt | ggctggcagc | tgctgcagtg | gctcctcatc | 420 |
| gccctccctg | ctaccttcgt | caacagtgcc | atccgttacc | tggagggcca | actgccctg | 480 |
| tcgttccgca | gccgtctggt | ggcccacgcc | taccgcctct | acttctccca | gcagacctac | 540 |
| taccgggtca | gcaacatgga | cgggcggctt | cgcaaccctg | accagtctct | gacggaggac | 600 |
| gtggtggcct | tgcggcctc | tgtggcccac | ctctactcca | acctgaccaa | gccactcctg | 660 |
| gacgtggctg | tgacttccta | caccctgctt | cgggcggccc | gctcccgtgg | agccggcaca | 720 |
| gcctggccct | cggccatcgc | cggcctcgtg | tgttcctca | cggccaacgt | gctgcgggcc | 780 |
| ttctcgccca | agttcgggga | gctggtggca | gaggaggcgc | ggcggaaggg | ggagctgcgc | 840 |
| tacatgcact | cgcgtgtggt | ggccaactcg | gaggagatcg | ccttctatgg | gggccatgag | 900 |
| gtggagctgg | ccctgctaca | gcgctcctac | caggacctgg | cctcgcagat | caacctcatc | 960 |
| cttctggaac | gccgtggta | tgttatgctg | agcagttcc | tcatgaagta | tgtgtggagc | 1020 |
| gcctcgggcc | tgctcatggt | ggctgtcccc | atcatcactg | ccactggcta | ctcagagtca | 1080 |
| gatgcagagg | ccgtgaagaa | ggcagccttg | aaaagaagg | aggaggagct | ggtgagcgag | 1140 |
| cgcacagaag | ccttcactat | tgcccgcaac | ctcctgacag | cggctgcaga | tgccattgag | 1200 |
| cggatcatgt | cgtcgtacaa | ggaggtgacg | gagctggctg | gctacacagc | ccgggtgcac | 1260 |
| gagatgttcc | aggtatttga | agatgttcag | cgctgtcact | tcaagaggcc | cagggagcta | 1320 |
| gaggacgctc | aggcggggtc | tgggaccata | ggccggtctg | tgtccgtgt | ggagggcccc | 1380 |
| ctgaagatcc | gaggccaggt | ggtggatgtg | aacaggggga | tcatctgcga | aacatcccc | 1440 |
| atcgtcacgc | cctcaggaga | ggtggtggtg | gccagcctca | acatcagggt | ggaggaaggc | 1500 |
| atgcatctgc | tcatcacagg | ccccaatggc | tgcggcaaga | gctccctgtt | ccggatcctg | 1560 |
| ggtgggctct | ggcccacgta | cggtggtgtg | ctctacaagc | ccccacccca | gcgcatgttc | 1620 |
| tacatcccgc | agaggcccta | catgtctgtg | ggctccctgc | gtgaccaggt | gatctacccg | 1680 |
| gactcagtgg | aggacatgca | aaggaagggc | tactcggagc | aggacctgga | agccatcctg | 1740 |
| gacgtcgtgc | acctgcacca | catcctgcag | cgggagggag | gttgggaggc | tatgtgtgac | 1800 |
| tggaaggacg | tcctgtcggg | tggcgagaag | cagagaatcg | gcatggcccg | catgttctac | 1860 |
| cacaggccca | agtacgccct | cctggatgaa | tgcaccagcg | ccgtgagcat | cgacgtggaa | 1920 |
| ggcaagatct | ccaggcggc | caaggacgcg | ggcattgccc | tgctctccat | cacccaccgg | 1980 |
| ccctcccctgt | ggaaatacca | cacacacttg | ctacagttcg | atggggaggg | cggctggaag | 2040 |
| ttcgagaagc | tggactcagc | tgcccgcctg | agcctgacgg | aggagaagca | gcggctggag | 2100 |
| cagcagctgg | cgggcattcc | caagatgcag | cggcgcctcc | aggagctctg | ccagatcctg | 2160 |
| ggcgaggcc | tggccccagc | gcatgtgccg | gcacctagcc | cgcaaggccc | tggtggcctc | 2220 |
| cagggtgcct | ccacctga | | | | | 2238 |

<210> SEQ ID NO 2
<211> LENGTH: 745
<212> TYPE: PRT
<213> ORGANISM: Homo sapiens

<400> SEQUENCE: 2

```
Met Pro Val Leu Ser Arg Pro Arg Pro Trp Arg Gly Asn Thr Leu Lys
1               5                   10                  15

Arg Thr Ala Val Leu Ala Leu Ala Ala Tyr Gly Ala His Lys Val
            20                  25                  30

Tyr Pro Leu Val Arg Gln Cys Leu Ala Pro Ala Arg Gly Leu Gln Ala
            35                  40                  45

Pro Ala Gly Glu Pro Thr Gln Glu Ala Ser Gly Val Ala Ala Ala Lys
        50                  55                  60

Ala Gly Met Asn Arg Val Phe Leu Gln Arg Leu Leu Trp Leu Leu Arg
65                  70                  75                  80

Leu Leu Phe Pro Arg Val Leu Cys Arg Glu Thr Gly Leu Leu Ala Leu
                85                  90                  95

His Ser Ala Ala Leu Val Ser Arg Thr Phe Leu Ser Val Tyr Val Ala
            100                 105                 110

Arg Leu Asp Gly Arg Leu Ala Arg Cys Ile Val Arg Lys Asp Pro Arg
            115                 120                 125

Ala Phe Gly Trp Gln Leu Leu Gln Trp Leu Leu Ile Ala Leu Pro Ala
        130                 135                 140

Thr Phe Val Asn Ser Ala Ile Arg Tyr Leu Glu Gly Gln Leu Ala Leu
145                 150                 155                 160

Ser Phe Arg Ser Arg Leu Val Ala His Ala Tyr Arg Leu Tyr Phe Ser
                165                 170                 175

Gln Gln Thr Tyr Tyr Arg Val Ser Asn Met Asp Gly Arg Leu Arg Asn
            180                 185                 190

Pro Asp Gln Ser Leu Thr Glu Asp Val Val Ala Phe Ala Ala Ser Val
            195                 200                 205

Ala His Leu Tyr Ser Asn Leu Thr Lys Pro Leu Leu Asp Val Ala Val
        210                 215                 220

Thr Ser Tyr Thr Leu Leu Arg Ala Ala Arg Ser Arg Gly Ala Gly Thr
225                 230                 235                 240

Ala Trp Pro Ser Ala Ile Ala Gly Leu Val Val Phe Leu Thr Ala Asn
                245                 250                 255

Val Leu Arg Ala Phe Ser Pro Lys Phe Gly Glu Leu Val Ala Glu Glu
            260                 265                 270

Ala Arg Arg Lys Gly Glu Leu Arg Tyr Met His Ser Arg Val Val Ala
            275                 280                 285

Asn Ser Glu Glu Ile Ala Phe Tyr Gly Gly His Glu Val Glu Leu Ala
        290                 295                 300

Leu Leu Gln Arg Ser Tyr Gln Asp Leu Ala Ser Gln Ile Asn Leu Ile
305                 310                 315                 320

Leu Leu Glu Arg Leu Trp Tyr Val Met Leu Glu Gln Phe Leu Met Lys
                325                 330                 335

Tyr Val Trp Ser Ala Ser Gly Leu Leu Met Val Ala Val Pro Ile Ile
            340                 345                 350

Thr Ala Thr Gly Tyr Ser Glu Ser Asp Ala Glu Ala Val Lys Lys Ala
            355                 360                 365

Ala Leu Glu Lys Lys Glu Glu Glu Leu Val Ser Glu Arg Thr Glu Ala
```

```
            370                 375                 380
Phe Thr Ile Ala Arg Asn Leu Leu Thr Ala Ala Asp Ala Ile Glu
385                 390                 395                 400

Arg Ile Met Ser Ser Tyr Lys Glu Val Thr Glu Leu Ala Gly Tyr Thr
                    405                 410                 415

Ala Arg Val His Glu Met Phe Gln Val Phe Glu Asp Val Gln Arg Cys
                420                 425                 430

His Phe Lys Arg Pro Arg Glu Leu Glu Asp Ala Gln Ala Gly Ser Gly
            435                 440                 445

Thr Ile Gly Arg Ser Gly Val Arg Val Glu Gly Pro Leu Lys Ile Arg
        450                 455                 460

Gly Gln Val Val Asp Val Glu Gln Gly Ile Ile Cys Glu Asn Ile Pro
465                 470                 475                 480

Ile Val Thr Pro Ser Gly Glu Val Val Ala Ser Leu Asn Ile Arg
                    485                 490                 495

Val Glu Glu Gly Met His Leu Leu Ile Thr Gly Pro Asn Gly Cys Gly
                500                 505                 510

Lys Ser Ser Leu Phe Arg Ile Leu Gly Gly Leu Trp Pro Thr Tyr Gly
            515                 520                 525

Gly Val Leu Tyr Lys Pro Pro Pro Gln Arg Met Phe Tyr Ile Pro Gln
        530                 535                 540

Arg Pro Tyr Met Ser Val Gly Ser Leu Arg Asp Gln Val Ile Tyr Pro
545                 550                 555                 560

Asp Ser Val Glu Asp Met Gln Arg Lys Gly Tyr Ser Glu Gln Asp Leu
                    565                 570                 575

Glu Ala Ile Leu Asp Val Val His Leu His His Ile Leu Gln Arg Glu
                580                 585                 590

Gly Gly Trp Glu Ala Met Cys Asp Trp Lys Asp Val Leu Ser Gly Gly
            595                 600                 605

Glu Lys Gln Arg Ile Gly Met Ala Arg Met Phe Tyr His Arg Pro Lys
        610                 615                 620

Tyr Ala Leu Leu Asp Glu Cys Thr Ser Ala Val Ser Ile Asp Val Glu
625                 630                 635                 640

Gly Lys Ile Phe Gln Ala Ala Lys Asp Ala Gly Ile Ala Leu Leu Ser
                    645                 650                 655

Ile Thr His Arg Pro Ser Leu Trp Lys Tyr His Thr His Leu Leu Gln
                660                 665                 670

Phe Asp Gly Glu Gly Gly Trp Lys Phe Glu Lys Leu Asp Ser Ala Ala
            675                 680                 685

Arg Leu Ser Leu Thr Glu Glu Lys Gln Arg Leu Glu Gln Gln Leu Ala
        690                 695                 700

Gly Ile Pro Lys Met Gln Arg Arg Leu Gln Glu Leu Cys Gln Ile Leu
705                 710                 715                 720

Gly Glu Ala Val Ala Pro Ala His Val Pro Ala Pro Ser Pro Gln Gly
                    725                 730                 735

Pro Gly Gly Leu Gln Gly Ala Ser Thr
                740                 745

<210> SEQ ID NO 3
<211> LENGTH: 1936
<212> TYPE: DNA
<213> ORGANISM: Artificial Sequence
<220> FEATURE:
<223> OTHER INFORMATION: human EF1alpha promoter
```

<400> SEQUENCE: 3

```
gctagcatgc ctaggtcgac caattctcat gtttgacagc ttatcatcga taagctttgg      60
agctaagcca gcaatggtag agggaagatt ctgcacgtcc cttccaggcg gcctccccgt     120
caccaccccc cccaacccgc cccgaccgga gctgagagta attcatacaa aaggactcgc     180
ccctgccttg gggaatccca gggaccgtcg ttaaactccc actaacgtag aacccagaga     240
tcgctgcgtt cccgcccct cacccgcccg ctctcgtcat cactgaggtg gagaagagca     300
tgcgtgaggc tccggtgccc gtcagtgggc agagcgcaca tcgcccacag tccccgagaa     360
gttggggga ggggtcggca attgaaccgg tgcctagaga aagtggcgcg gggtaaactg     420
ggaaagtgat gtcgtgtact ggctccgcct ttttcccgag ggtgggggag aaccgtatat     480
aagtgcagta gtcgccgtga acgttctttt tcgcaacggg tttgccgcca gaacacaggt     540
aagtgccgtg tgtggttccc gcgggcctgg cctctttacg ggttatggcc cttgcgtgcc     600
ttgaattact tccacgcccc tggctgcagt acgtgattct tgatcccgag cttcggtttg     660
gaagtgggtg gagagttcg aggccttgcg cttaaggagc cccttcgcct cgtgcttgag     720
ttgaggcctg gcctgggcgc tggggccgcc gcgtgcgaat ctggtggcac cttcgcgcct     780
gtctcgctgc tttcgataag tctctagcca tttaaaattt ttgatgacct gctgcgacgc     840
ttttttctg gcaagatagt cttgtaaatg cgggccaaga tctgcacact ggtatttcgg     900
ttttgggc cgcgggcggc gacggggccc gtgcgtccca gcgcacatgt tcggcgaggc     960
ggggcctgcg agcgcggcca ccgagaatcg gacggggta gtctcaagct ggccggcctg    1020
ctctggtgcc tggcctcgcg ccgccgtgta tcgccccgcc ctgggcggca aggctggccc    1080
ggtcggcacc agttgcgtga gcggaaagat ggccgcttcc cggccctgct gcagggagct    1140
caaaatggag gacgcggcgc tcgggagagc gggcgggtga gtcacccaca caaggaaaa    1200
gggcctttcc gtcctcagcc gtcgcttcat gtgactccac ggagtaccgg gcgccgtcca    1260
ggcacctcga ttagttctcg agcttttgga gtacgtcgtc tttaggttgg ggggagggt    1320
tttatgcgat ggagtttccc cacactgagt gggtggagac tgaagttagg ccagcttggc    1380
acttgatgta attctccttg gaatttgccc tttttgagtt tggatcttgg ttcattctca    1440
agcctcagac agtggttcaa agttttttc ttccatttca ggtgtcgtga aaactctaga    1500
gcggccgcgg aggccgaatt cccgggatat cgtcgacgcc aggctgcgga gcggacggac    1560
gcgcctggtg ccccggggag gggcgccacc ggggggaggag gaggaggaga aggtggagag    1620
gaagagacgc cccctctgcc cgagacctct caaggccctg acctcagggg ccagggcact    1680
gacaggacag gagagccaag ttcctccact tgggctgccc gaagaggccg cgaccctgga    1740
gggccctgag cccaccgcac caggggcccc agcaccaccc cggggggccta aagcgacagt    1800
ctcaggggcc atcgcaaggt ttccagttgc ctagacaaca ggcccagggt cagagcaaca    1860
atccttccag ccacctgcct caactgctgc cccaggcacc agcccagtc cctacgcggc    1920
agccagccca ggtgac                                                  1936
```

<210> SEQ ID NO 4
<211> LENGTH: 4174
<212> TYPE: DNA
<213> ORGANISM: Artificial Sequence
<220> FEATURE:
<223> OTHER INFORMATION: DNA sequence of EF1alpha promoter and ABCD1

<400> SEQUENCE: 4

```
gctagcatgc ctaggtcgac caattctcat gtttgacagc ttatcatcga taagctttgg      60
```

```
agctaagcca gcaatggtag agggaagatt ctgcacgtcc cttccaggcg gcctcccgt    120 caccacccc cccaacccgc cccgaccgga gctgagagta attcatacaa aaggactcgc    180
ccctgccttg gggaatccca gggaccgtcg ttaaactccc actaacgtag aacccagaga    240
tcgctgcgtt cccgccccct cacccgcccg ctctcgtcat cactgaggtg gagaagagca    300
tgcgtgaggc tccggtgccc gtcagtgggc agagcgcaca tcgcccacag tccccgagaa    360 gttggggga gggtcggca attgaaccgg tgcctagaga agtggcgcg gggtaaactg       420 ggaaagtgat gtcgtgtact ggctccgcct ttttcccgag ggtgggggag aaccgtatat    480
aagtgcagta gtcgccgtga acgttctttt tcgcaacggg tttgccgcca gaacacaggt    540
aagtgccgtg tgtggttccc gcgggcctgg cctctttacg ggttatggcc cttgcgtgcc    600
ttgaattact tccacgcccc tggctgcagt acgtgattct tgatcccgag cttcgggttg    660
gaagtgggtg ggagagttcg aggccttgcg cttaaggagc cccttcgcct cgtgcttgag    720
ttgaggcctg gcctgggcgc tggggccgcc gcgtgcgaat ctggtggcac cttcgcgcct    780
gtctcgctgc tttcgataag tctctagcca tttaaaattt ttgatgacct gctgcgacgc    840 ttttttctg gcaagatagt cttgtaaatg cgggccaaga tctgcacact ggtatttcgg     900 tttttgggc cgcgggcggc gacggggccc gtgcgtccca gcgcacatgt tcggcgaggc     960
ggggcctgcg agcgcggcca ccgagaatcg gacggggta gtctcaagct ggccggcctg    1020
ctctggtgcc tggcctcgcg ccgccgtgta tcgccccgcc ctgggcggca aggctggccc    1080
ggtcggcacc agttgcgtga gcggaaagat ggccgcttcc cggccctgct gcagggagct    1140
caaaatggag gacgcggcgc tcgggagagc gggcgggtga gtcacccaca caaaggaaaa    1200
gggcctttcc gtcctcagcc gtcgcttcat gtgactccac ggagtaccgg gcgccgtcca    1260
ggcacctcga ttagttctcg agcttttgga gtacgtcgtc tttaggttgg ggggaggggt    1320
tttatgcgat ggagtttccc cacactgagt gggtggagac tgaagttagg ccagcttggc    1380
acttgatgta attctccttg gaatttgccc tttttgagtt tggatcttgg ttcattctca    1440
agcctcagac agtggttcaa agttttttttc ttccatttca ggtgtcgtga aaactctaga    1500
gcggccgcgg aggccgaatt cccgggatat cgtcgacgcc aggctgcgga gcggacggac    1560
gcgcctggtg cccgggggag gggcgccacc gggggaggag gaggaggaga aggtggagag    1620
gaagagacgc cccctctgcc cgagacctct caaggccctg acctcagggg ccagggcact    1680
gacaggacag gagagccaag ttcctccact tgggctgccc gaagaggccg cgaccctgga    1740
gggccctgag cccaccgcac caggggcccc agcaccaccc cggggggccta aagcgacagt    1800 ctcaggggcc atcgcaaggt ttccagttgc ctagacaaca ggcccagggt cagagcaaca    1860
atccttccag ccacctgcct caactgctgc cccaggcacc agcccagtc cctacgcggc      1920 agccagccca ggtgacatgc cggtgctctc caggccccgg ccctggcggg ggaacacgct    1980
gaagcgcacg gccgtgctcc tggccctcgc ggcctatgga gcccacaaag tctacccctt    2040
ggtgcgccag tgcctggccc cggccagggg tcttcaggcg cccgccgggg agcccacgca    2100
ggaggcctcc ggggtcgcgg cggccaaagc tggcatgaac cgggtattcc tgcagcggct    2160 cctgtgctc ctgcggctgc tgttccccg gtcctgtgc cggagacgg ggctgctggc       2220 cctgcactcg gccgccttgg tgagccgcac cttcctgtcg gtgtatgtgg cccgcctgga    2280
cggaaggctg gcccgctgca tcgtccgcaa ggacccgcgg gcttttggct ggcagctgct    2340
gcagtggctc ctcatcgccc tccctgctac cttcgtcaac agtgccatcc gttacctgga    2400
```

```
gggccaactg gccctgtcgt tccgcagccg tctggtggcc cacgcctacc gcctctactt    2460
ctcccagcag acctactacc gggtcagcaa catggacggg cggcttcgca accctgacca    2520
gtctctgacg gaggacgtgg tggcctttgc ggcctctgtg gcccacctct actccaacct    2580
gaccaagcca ctcctggacg tggctgtgac ttcctacacc ctgcttcggg cggcccgctc    2640
ccgtggagcc ggcacagcct ggccctcggc catcgccggc ctcgtggtgt tcctcacggc    2700
caacgtgctg cgggccttct cgcccaagtt cggggagctg gtggcagagg aggcgcggcg    2760
gaagggggag ctgcgctaca tgcactcgcg tgtggtggcc aactcggagg agatcgcctt    2820
ctatggggc catgaggtgg agctggccct gctacagcgc tcctaccagg acctggcctc    2880
gcagatcaac ctcatccttc tggaacgcct gtggtatgtt atgctggagc agttcctcat    2940
gaagtatgtg tggagcgcct cgggcctgct catggtggct gtccccatca tcactgccac    3000
tggctactca gagtcagatg cagaggccgt gaagaaggca gccttggaaa agaaggagga    3060
ggagctggtg agcgagcgca cagaagcctt cactattgcc cgcaacctcc tgacagcggc    3120
tgcagatgcc attgagcgga tcatgtcgtc gtacaaggag gtgacggagc tggctggcta    3180
cacagcccgg gtgcacgaga tgttccaggt atttgaagat gttcagcgct gtcacttcaa    3240
gaggcccagg gagctagagg acgctcaggc ggggtctggg accataggcc ggtctggtgt    3300
ccgtgtggag ggcccctga agatccgagg ccaggtggtg gatgtggaac aggggatcat    3360
ctgcgagaac atccccatcg tcacgccctc aggagaggtg gtggtggcca gcctcaacat    3420
cagggtggag gaaggcatgc atctgctcat cacaggcccc aatggctgcg gcaagagctc    3480
cctgttccgg atcctgggtg ggctctgcc cacgtacggt ggtgtgctct acaagccccc    3540
accccagcgc atgttctaca tcccgcagag gccctacatg tctgtgggct ccctgcgtga    3600
ccaggtgatc tacccggact cagtggagga catgcaaagg aagggctact cggagcagga    3660
cctggaagcc atcctggacg tcgtgcacct gcaccacatc ctgcagcggg agggaggttg    3720
ggaggctatg tgtgactgga aggacgtcct gtcgggtggc gagaagcaga gaatcggcat    3780
ggcccgcatg ttctaccaca ggcccaagta cgccctcctg gatgaatgca ccagcgccgt    3840
gagcatcgac gtggaaggca agatcttcca ggcggccaag gacgcgggca ttgccctgct    3900
ctccatcacc caccggccct ccctgtggaa ataccacaca cacttgctac agttcgatgg    3960
ggagggcggc tggaagttcg agaagctgga ctcagctgcc cgcctgagcc tgacggagga    4020
gaagcagcgg ctggagcagc agctggcggg cattcccaag atgcagcggc gcctccagga    4080
gctctgccag atcctgggcg aggccgtggc cccagcgcat gtgccggcac ctagcccgca    4140
aggccctggt ggcctccagg gtgcctccac ctga                                4174
```